US008798708B2

(12) United States Patent
Tremblay (10) Patent No.: US 8,798,708 B2
(45) Date of Patent: Aug. 5, 2014

(54) PHYSIOLOGICAL SENSOR PLACEMENT AND SIGNAL TRANSMISSION DEVICE (75) Inventor: Kathleen Tremblay, Westfield, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/424,653

(22) Filed: Mar. 20, 2012

(65) Prior Publication Data

US 2013/0072777 A1 Mar. 21, 2013

Related U.S. Application Data (63) Continuation of application No. 11/904,754, filed on Sep. 28, 2007, now abandoned.

(51) Int. Cl.
*A61B 5/0408* (2006.01)
*A61N 1/04* (2006.01)

(52) U.S. Cl.
USPC ............ 600/388; 600/509; 600/394; 607/149

(58) Field of Classification Search
USPC .................. 600/386, 388–390, 394, 382, 509; 439/909; 607/149
See application file for complete search history.

(56) References Cited

U.S. PATENT DOCUMENTS

| | | | |
|---|---|---|---|
| 3,752,151 A | 8/1973 | Robichaud |
| 3,805,769 A | 4/1974 | Sessions |
| 3,828,766 A | 8/1974 | Krasnow |
| 3,868,946 A | 3/1975 | Hurley |
| 3,888,240 A | 6/1975 | Reinhold, Jr. et al. |
| 3,901,218 A | 8/1975 | Buchalter |
| 3,998,213 A | 12/1976 | Price |
| 4,027,664 A | 6/1977 | Heavner, Jr. et al. |
| 4,034,854 A | 7/1977 | Bevilacqua |
| 4,077,397 A | 3/1978 | Ellis et al. |
| 4,121,575 A | 10/1978 | Mills et al. |
| 4,202,344 A | 5/1980 | Mills et al. |
| 4,353,372 A | 10/1982 | Ayer |
| 4,365,634 A | 12/1982 | Bare et al. |
| 4,498,480 A | 2/1985 | Mortensen |
| 4,729,377 A | 3/1988 | Granek et al. |

(Continued)

FOREIGN PATENT DOCUMENTS

| | | |
|---|---|---|
| DE | 102004032410 | 1/2006 |
| EP | 0766946 | 4/1997 |
| EP | 1050269 | 11/2000 |

OTHER PUBLICATIONS

International Search Report EP07253850 dated Dec. 21, 2007.

(Continued)

*Primary Examiner* — Lee S Cohen
*Assistant Examiner* — Erin M Cardinal
(74) *Attorney, Agent, or Firm* — Lisa E. Winsor, Esq.

(57) ABSTRACT

A garment is used to facilitate the placement of biomedical sensors or other electrodes on the body. The garment is comfortable and allows freedom of movement much like typical clothing. Textile based electrical components are included in the garment which are capable of transmitting an electrical signal to and from various external electrodes placed on the body. A textile based EMI shield protects the signals from electromagnetic interference. The garment may take any form such as a vest, sports bra, long sleeve shirt, bonnet, or other form and may provide access to an electrode placement site without requiring removal of the garment.

19 Claims, 5 Drawing Sheets

(56) References Cited

U.S. PATENT DOCUMENTS

| | | |
|---|---|---|
| 4,763,660 A | 8/1988 | Kroll et al. |
| 4,781,200 A | 11/1988 | Baker |
| 4,785,822 A | 11/1988 | Wallace |
| 4,815,964 A | 3/1989 | Cohen et al. |
| 4,909,260 A | 3/1990 | Salem et al. |
| 4,947,846 A | 8/1990 | Kitagawa et al. |
| 4,957,109 A | 9/1990 | Groeger et al. |
| 5,224,479 A * | 7/1993 | Sekine .......................... 600/389 |
| 5,263,481 A | 11/1993 | Axelgaard |
| 5,341,806 A | 8/1994 | Gadsby et al. |
| 5,353,793 A | 10/1994 | Bornn |
| 5,370,116 A | 12/1994 | Rollman et al. |
| 5,405,269 A | 4/1995 | Stupecky |
| 5,507,290 A | 4/1996 | Kelly et al. |
| 5,511,553 A | 4/1996 | Segalowitz |
| 5,546,950 A | 8/1996 | Schoeckert et al. |
| 5,582,180 A | 12/1996 | Manset et al. |
| 5,622,168 A | 4/1997 | Keusch et al. |
| 5,685,303 A | 11/1997 | Rollman et al. |
| 5,704,351 A | 1/1998 | Mortara et al. |
| 5,724,984 A | 3/1998 | Arnold et al. |
| 5,813,979 A | 9/1998 | Wolfer |
| 5,865,740 A | 2/1999 | Kelly et al. |
| 5,865,741 A | 2/1999 | Kelly et al. |
| 5,913,834 A | 6/1999 | Francais |
| 5,916,159 A | 6/1999 | Kelly et al. |
| 5,938,597 A | 8/1999 | Stratbucker |
| 6,006,125 A | 12/1999 | Kelly et al. |
| 6,032,064 A | 2/2000 | Devlin et al. |
| 6,055,448 A | 4/2000 | Anderson et al. |
| 6,066,093 A | 5/2000 | Kelly et al. |
| 6,115,623 A | 9/2000 | McFee |
| 6,122,536 A | 9/2000 | Sun et al. |
| 6,122,544 A | 9/2000 | Organ |
| 6,157,851 A | 12/2000 | Kelly et al. |
| 6,219,568 B1 | 4/2001 | Kelly et al. |
| 6,219,569 B1 | 4/2001 | Kelly et al. |
| 6,232,366 B1 | 5/2001 | Wang et al. |
| 6,240,323 B1 | 5/2001 | Calenzo, Sr. et al. |
| 6,304,783 B1 | 10/2001 | Lyster et al. |
| 6,339,720 B1 | 1/2002 | Anzellini et al. |
| 6,341,504 B1 | 1/2002 | Istook |
| 6,360,119 B1 | 3/2002 | Roberts |
| 6,400,977 B1 | 6/2002 | Kelly et al. |
| 6,453,186 B1 | 9/2002 | Lovejoy et al. |
| 6,456,872 B1 | 9/2002 | Faisandier |
| 6,553,246 B1 | 4/2003 | Wenger |
| 6,553,250 B2 | 4/2003 | Rantala |
| 6,564,079 B1 | 5/2003 | Cory et al. |
| 6,611,705 B2 | 8/2003 | Hopman et al. |
| 6,623,312 B2 | 9/2003 | Merry et al. |
| 6,636,754 B1 | 10/2003 | Baura et al. |
| 6,647,286 B1 | 11/2003 | Kato et al. |
| 6,654,626 B2 | 11/2003 | Devlin et al. |
| 6,748,797 B2 | 6/2004 | Breed et al. |
| 6,751,493 B2 | 6/2004 | Wenger |
| 6,768,921 B2 | 7/2004 | Organ et al. |
| 6,816,744 B2 | 11/2004 | Garfield et al. |
| 6,847,836 B1 | 1/2005 | Sujdak |
| 6,970,731 B1 | 11/2005 | Jayaraman et al. |
| 6,973,341 B2 | 12/2005 | Watson |
| 6,973,343 B2 | 12/2005 | Wenger |
| 6,980,852 B2 | 12/2005 | Jersey-Willuhn et al. |
| 7,104,801 B1 | 9/2006 | Brodnick et al. |
| 7,150,655 B2 | 12/2006 | Mastrototaro et al. |
| 7,169,107 B2 | 1/2007 | Jersey-Willuhn et al. |
| 7,184,820 B2 | 2/2007 | Jersey-Willuhn et al. |
| 7,197,357 B2 | 3/2007 | Istvan et al. |
| 7,272,428 B2 | 9/2007 | Hopman et al. |
| 7,319,895 B2 | 1/2008 | Klefstad-Sillonville et al. |
| 7,333,850 B2 | 2/2008 | Marossero et al. |
| 2002/0072682 A1* | 6/2002 | Hopman et al. ............. 600/509 |
| 2002/0133069 A1 | 9/2002 | Roberts |
| 2002/0138125 A1* | 9/2002 | Axelgaard et al. ............ 607/149 |
| 2002/0188216 A1 | 12/2002 | Kayyali et al. |
| 2004/0073127 A1 | 4/2004 | Istvan et al. |
| 2004/0127802 A1 | 7/2004 | Istvan et al. |
| 2004/0176674 A1 | 9/2004 | Nazeri |
| 2005/0010096 A1* | 1/2005 | Blackadar .................... 600/388 |
| 2005/0034485 A1* | 2/2005 | Klefstad-Sillonville et al. .............................. 66/171 |
| 2005/0054941 A1* | 3/2005 | Ting et al. ..................... 600/529 |
| 2005/0177052 A1 | 8/2005 | Istvan et al. |
| 2005/0203349 A1 | 9/2005 | Nanikashvili |
| 2006/0073728 A1 | 4/2006 | Zaiken et al. |
| 2006/0111640 A1* | 5/2006 | Shen et al. .................... 600/509 |
| 2006/0117805 A1 | 6/2006 | Valentine et al. |
| 2007/0038057 A1 | 2/2007 | Nam et al. |
| 2007/0260133 A1 | 11/2007 | Meyer |
| 2008/0091097 A1* | 4/2008 | Linti et al. .................... 600/389 |
| 2008/0143080 A1 | 6/2008 | Burr |
| 2009/0088652 A1 | 4/2009 | Tremblay |
| 2011/0288604 A1* | 11/2011 | Kaib et al. ........................ 607/5 |

OTHER PUBLICATIONS

International Search Report EP07251765 dated Mar. 31, 2008.
International Search Report EP07254691 dated Mar. 25, 2008.
International Search Report EP08164409 dated Jan. 27, 2009.
Andreas Boos et al.; "A New Lightweight Fetal Telemetry System"; Dec. 1995; Hewlett-Packard Journal; pp. 82-93.
Office Action dated Jun. 15, 2011; for U.S. Appl. No. 11/904,754; 21 pages.
Response filed Sep. 15, 2011; for Office Action dated Jun. 15, 2011; for U.S. Appl. No. 11/904,754; 18 pages.
Final Office Action dated Nov. 15, 2011; for U.S. Appl. No. 11/904,754; 12 pages.

* cited by examiner

PHYSIOLOGICAL SENSOR PLACEMENT AND SIGNAL TRANSMISSION DEVICE

CROSS-REFERENCE TO RELATED APPLICATIONS

This application is a continuation application of and claims priority under 35 U.S.C. §120 to U.S. application Ser. No. 11/904,754 filed on Sep. 28, 2007, entitled PHYSIOLOGICAL SENSOR PLACEMENT AND SIGNAL TRANSMISSION DEVICE, and which is now abandoned, the entire contents of which are incorporated herein by reference for all purposes.

BACKGROUND

1. Technical Field

The present disclosure relates to the monitoring and transmission of electrical signals for medical purposes. In particular the disclosure relates to a garment capable of transmitting electrical signals such as biopotential signals from ECG electrodes.

2. Background of Related Art

Electrocardiograph (ECG) monitors and recorders are widely used to obtain medical signals containing information indicative of the electrical activity associated with the heart and pulmonary system. To obtain these biopotential signals, electrodes are applied to the skin of a patient or other subject in various locations and coupled to an ECG monitor. The number of electrodes applied and placement locations of the electrodes are dependant on the type of information sought by the clinician.

Conventional electrocardiography protocols have established several standard lead configurations for the placement of ECG electrodes on the subject's skin. A standard 3-lead configuration, for example, requires the placement of three electrodes; one adjacent to each clavicle bone on the upper chest and a third adjacent to the lower left abdomen. A standard 12-lead configuration requires the placement of ten electrodes; six are placed at various locations on the patient's chest near the heart, and four are placed to represent each of the subject's limbs. The right leg electrode is typically designated as the ground, and twelve measurements are then taken from the ten electrodes. These measurements include six measurements from the six chest electrodes, three measurements of the difference in potential between two limbs, and three measurements of the difference between the potential at one limb and the average of the potentials at two other limbs. In addition to the 3-lead and 12-lead configurations, other standard configurations have been developed. The most prevalent among these are the 5-lead and 7-lead configurations.

Once placed on the skin of the subject, electrodes are normally connected to a lead set which is then connected to an ECG monitor. The ECG monitor receives the biopotential signals from the body and processes the data such that the information can be interpreted by a clinician. The quality of information produced is dependant on several factors. Among these are the proper placement of the electrodes, consistent placement of the electrodes relative to one another and proper connection of the lead set to the proper electrodes.

A clinician may find it cumbersome to make the proper connections with a lead set involving many wires which often tangle, and may find it difficult to determine exactly which individual wire is to be connected at which point. Also, a subject will often experience discomfort while connected to a traditional lead set. The subject's movement may be limited and the wires may cause some skin irritation.

SUMMARY

There is a need for an apparatus to alleviate some of the difficulties involved with a traditional ECG lead set. Accordingly, the present disclosure is directed to an apparatus for facilitating the connection of a biomedical electrode array to a monitoring, diagnostic, or stimulating device. The apparatus includes a garment member that may be positioned on a body portion of a subject. At least one signal transmission pathway is formed in the garment member and includes a conductive thread passed through the garment member to connect the signal transmission pathway to the garment member. The signal transmission pathway has a first end connectable to a biomedical electrode a second end connectable to a monitoring, diagnostic, or stimulating device. The signal transmission pathway is adapted for transmitting signals between the biomedical electrode and the monitoring, diagnostic or stimulating device.

Developments in electrically conductive fibers and textiles have made it possible to incorporate a variety of electronics including, as will be discussed herein, signal transmission pathways directly into wearable clothing. Metallic fibers with a very low resistance to electrical current may be woven into otherwise non-conductive fabrics allowing the fibers to be individually addressed like the wires in a cable. These conductive fibers may carry data signals or power and allow for the connection of traditional electrical components by conventional means. Furthermore, traditional stitching techniques such as embroidery may be used with electrically conductive threads to create electrical traces. Some of these devices may even be designed to withstand the stress of laundering.

The present disclosure describes a garment providing a means for the simple connection to externally placed physiological sensors on the human body that can transmit electronic signals to and from the body. The garment is also equipped with an EMI shield which protects the signal transmission pathways from the interference associated with electromagnetic fields. The garment is either disposable or washable.

The garment includes a comfort layer which is described as the garment member herein. The garment member provides a substrate or a canvas to which conductive thread, connectors, adapters, an EMI shield or other components may be affixed. Connectors are provided at various locations on the garment member which provide a connection means to physiological sensors or other externally placed electrodes on the body. The connectors are electrically attached to signal transmission pathways formed from a conductive thread stitched into the garment member. The signal transmission pathways lead to an adapter or adapters which provide a connection means to external monitoring or stimulating equipment. Finally, the signal transmission pathways are covered on the interior and exterior surface of the garment member by an EMI shield formed from a wearable fabric.

In one embodiment, the garment member takes the form of a vest or shirt which may be worn during ECG monitoring. Conductive thread is stitched into the garment member in a pattern that allows biopotential signals from standard 3, 5, 7, or 12-lead configurations to be transmitted to an adapter at the waist of the subject. The signal transmission pathways are stitched in a pattern such that each pathway is isolated from the others and each pathway is covered by a fabric based EMI shield. The garment member is made from a light weight material such as cotton or polyester providing the subject with comfort and ease of movement without undue pulling on the sensor sites.

In another embodiment, the garment member takes the form of a full length sports bra. This embodiment naturally lifts the breasts and allows a clinician to correctly place electrode leads in the area underneath the breasts. Another embodiment is a bonnet worn over the head to obtain electroencephalography (EEG) signals. Still another embodiment is a shirt with full length sleeves. This embodiment allows for sensors such as pulse oximetry probes, temperature probes and glucose monitors to be placed on the hands and wrists.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

The exemplary embodiments of the apparatus disclosed herein are discussed in terms of performing a diagnostic or therapeutic procedure involving collecting or delivering electrical signals relative to a subject. Such procedures are inclusive of, but, not limited to electrocardiograph procedures, maternal and/or fetal monitoring, and a variety of signal based rehabilitative procedures. However, it is envisioned that the present disclosure may be employed with many applications including surgical, diagnostic, and related treatments of diseases and body ailments of a subject.

In the discussion that follows, the term "subject" refers to a human patient or other animal. The term "clinician" refers to a doctor, nurse, or other care provider and may include support personnel.

Figures 1A, 1B:
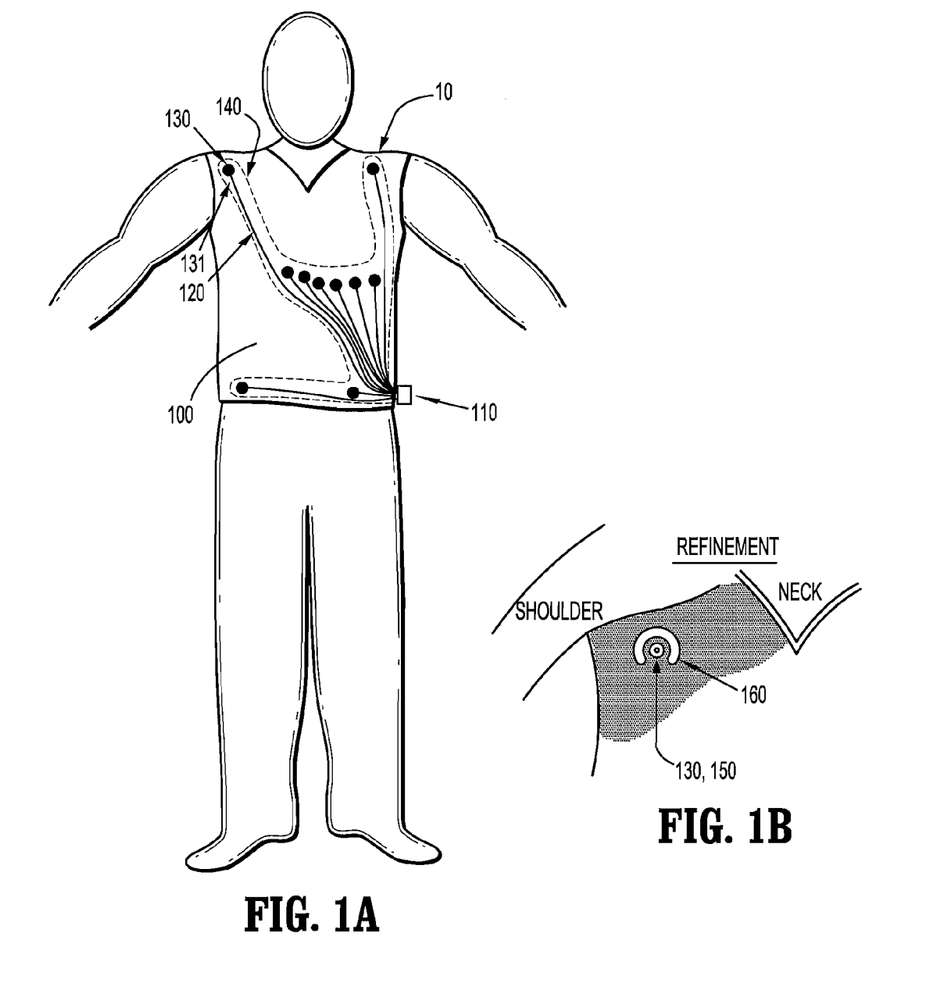
FIG. 1A is a front view of an embodiment of the present disclosure as a vest on a subject.
FIG. 1B is an enlarged view of a sensor site depicting a flap refinement of the vest depicted in FIG. 1.

Referring initially to FIG. 1A, an embodiment of the present invention is depicted as a vest 10 donned by a subject. Vest 10 has application in at least 3, 5, 7, or 12-lead ECG monitoring systems and is depicted here in a 12-lead system. The vest includes a garment member 100, an adapter 110, several connectors 130, several signal transmission pathways 120 connecting the adapter to the several connectors, and an EMI shield 140 covering the signal transmission pathways. The garment member 100 may be made from a non-conductive lightweight material such as cotton or polyester. This layer provides the subject the comfort and ease of movement that is provided by typical clothing while providing a substrate for the other components. Connectors 130 are positioned throughout the vest 10 at sensor sites where an external electrode may be placed on the body of the subject. The sensor sites are selected appropriately for the particular type of signal to be monitored or transmitted through the electrode, and each electrode may be selected individually to transmit a different type of signal. The connectors 130 are adapted to make physical contact with the leads of the electrodes and ensure electrical continuity therewith. Connectors may be any industry standard devices such as snaps, pinch-clips and alligator clips may be appropriate selections for connectors 130. Each connector will likely have leads (or another interface) opposite the functional end which will be attached to the signal transmission pathways 120.

Figure 1C:
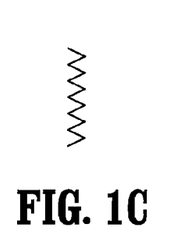
FIG. 1C-FIG. 1F depict exemplary stitch patterns which may be suitable to create the signal transmission pathways of FIG. 1A.
Figure 1D:
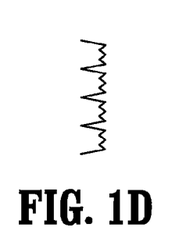
Figure 1E:
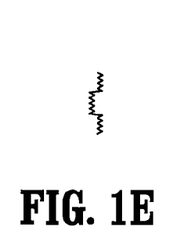
Figure 1F:
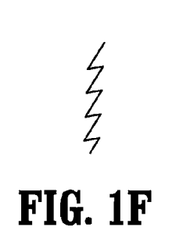

The leads 131 of the connectors 130 may be attached to the first ends of signal transmission pathways 120 by stitching the leads onto the garment member 100 using a conductive thread. As used herein, the term "stitching" includes any type of sewing or needlework in which a flexible fiber or bundle of fibers is passed through a substrate connecting the fiber or bundle of fibers to the substrate. This includes embroidery, needle-punching and the like. Here, the leads are stitched to the garment member 100 with a conductive thread to ensure electrical continuity with the conductive thread. This may be the only means by which the connector is affixed to the garment member. Alternatively, additional non-conductive stitching or other conventional means may be used in combination. The conductive stitching is continued in a direction toward the adapter 110 to form the signal transmission pathway 120. The stitching for the signal transmission pathway 120 may take the form of a zig-zag stitch where the conductive thread is shifted laterally with respect to the general direction of the pathway as shown in FIG. 1C. This type of stitching may allow the garment member 100 to maintain much of its inherent flexibility. Other types of stitches which can accomplish this include, but are not limited to, an elastic blind hem stitch (FIG. 1D), a platform stitch (FIG. 1E), and stem stitch (FIG. 1F). Regardless of the type of stitching selected, each signal transmission pathway 120 should be isolated spatially and electrically from the other pathways. The conductive stitching may again be used at the second ends of signal transmission pathways 120 to affix the leads or interface of the adapter to the garment member. Alternatively the adapter 110 may be a clam-shell design that clamps over the conductive threads. In this way, the electrical continuity may be established between the electrodes on the body of the subject and the adapter 110. The adapter 110 may then be connected to external monitoring or stimulating equipment establishing electrical continuity between the subject and the external equipment.

The conductive thread used can be any number of materials commonly used in the garment industry for decorative purposes containing conductive media such as silver, copper, nickel, and carbon. Commercially available products include a variety of threads with the flexibility, durability and low electrical resistance which are suitable for creating a signal transmission pathway 120.

Finally FIG. 1A depicts an EMI shield 140 covering the connectors 130 and signal transmission pathways 120. As shown a single piece of EMI shielding cloth is affixed to the garment member 100 covering each of the connectors 130 and signal transmission pathways 120, but it is to be understood that each component may have its own shield. An appropriate EMI shield will be selected primarily to prevent interference from electromagnetic fields in the signal transmission pathway 120. A textile based EMI shield might consist of a weave of cotton and metallic fibers wherein the metallic fibers constitute an appropriate proportion of the weight of the fabric. The fabric should be capable of redirecting a magnetic flux away from the signal transmission pathways 120, have the normal qualities of clothing and be suitable for the fabrication of garments normally worn in contact with the skin. With reference to FIG. 1B, connector 130 is positioned in a flap 150 near the sensor site. Flap 150 at least partially covers an aperture 160 in the garment member which surrounds the sensor site. Because of the inherent flexibility in material composing the garment member, flap 150 is movable between a position wherein the flap substantially covers the aperture 160, and a position where the aperture is left substantially uncovered. This flap and aperture arrangement allows a clinician to view the electrode placement on the skin, or attach or remove an electrode without removing the garment. Additionally this provides strain relief to the electrode by reducing the multi-directional pull exerted by the garment.

Figure 2A:
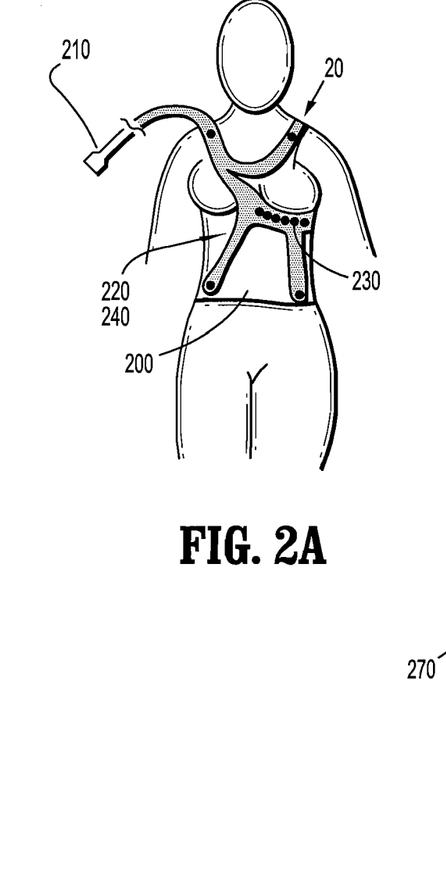
FIG. 2A is a front view of an embodiment of the invention as a full length sports bra on a subject.

Referring now to FIG. 2A, an embodiment of the present invention is depicted as a full length sports bra 20 donned by a subject. The sports bra includes a garment member 200, an adapter 210, several connectors 230, several signal transmission pathways 220 connecting the adapter to the several connectors, and an EMI shield 240 covering the signal transmission pathways.

Figure 2B:
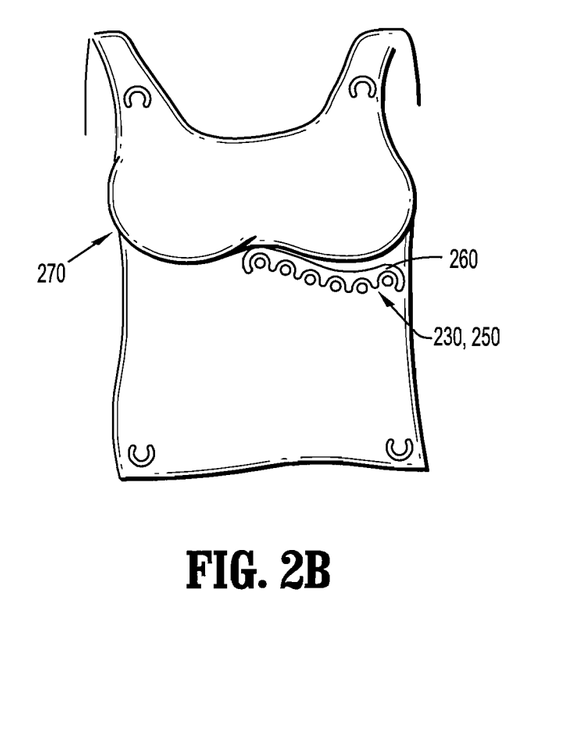
FIG. 2B is an enlarged view of the sports bra of FIG. 2A depicting a refinement.

As indicated in FIG. 2B, the bra portion of the garment naturally lifts the breasts with a support means 270. Support means 270 may be an underwire or elastic member which provides access to an aperture 260 under the left breast. The garment then frees the clinician from having to lift the breast, which clinicians often feel uncomfortable doing, and enables clinician to properly place electrodes in the area. Also evident from FIG. 2B is that aperture 260 may encompass several sensor sites and accommodate multiple flaps 250 and connectors 230.

Figure 3A:
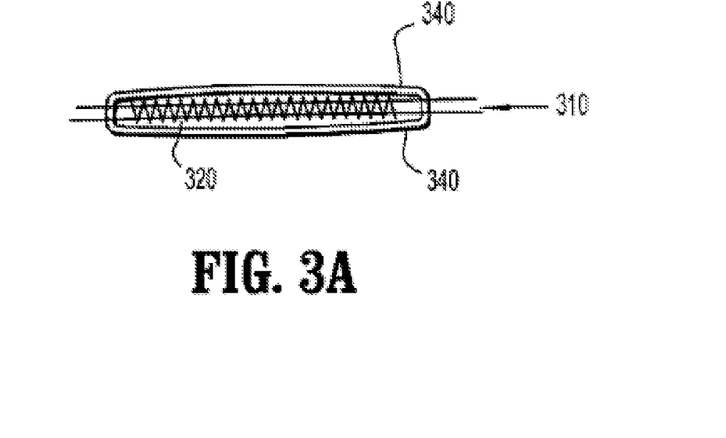
FIG. 3A is a cross-sectional view of signal a transmission pathway protected with an EMI shield.
Figure 3B:
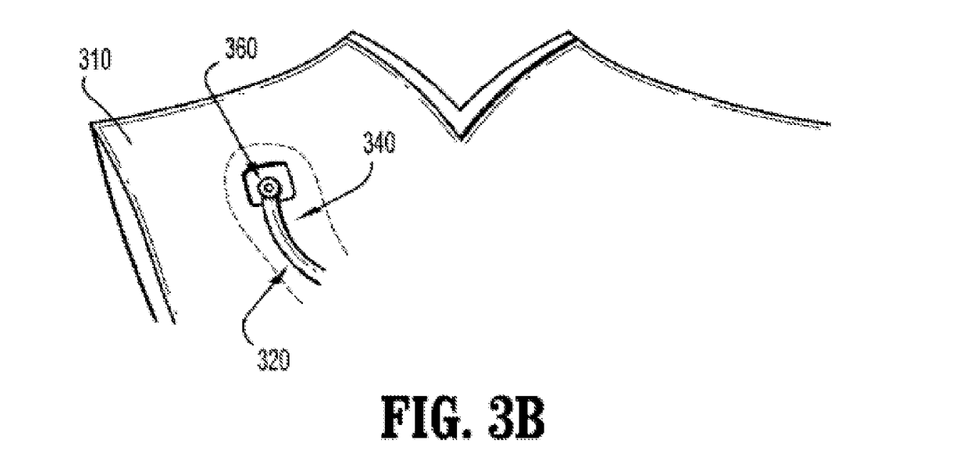
FIG. 3B is a view similar to view 1B depicting the EMI shield used in conjunction with the flap refinement.

Referring now to FIG. 3A, a cross section of transmission pathway 320 is depicted. Conductive stitching forms the transmission pathway 320 which protrudes on each side of garment member 310. A fabric EMI shield 340 is placed on both sides of the signal transmission pathway 320 so that one shield is located on the interior of the garment and another on the exterior. For this reason, it is desirable that the shield on the interior feel comfortable against the skin of the subject. Finally, FIG. 3B depicts an aperture 360 which extends through garment member 310 and both layers of EMI shield 340. The signal transmission pathway 320 extends from the aperture in the normal manner.

Other embodiments of the present invention include a bonnet worn over the head to obtain EEG signals, a shirt with full length sleeves allowing for sensors such as pulse oximetry probes, temperature probes and glucose monitors to be placed on the hands and wrists, or even a simple substantially flat patch which may be affixed anywhere on the body with an appropriate strap or adhesive. Any of these embodiments may include a fabric tab disposed within the adapter which is long enough when extended to allow the garment to be plugged into external equipment. Alternatively, an OEM equipment cable may be disposed within the adapter.

Figures 4A, 4B, 4C:
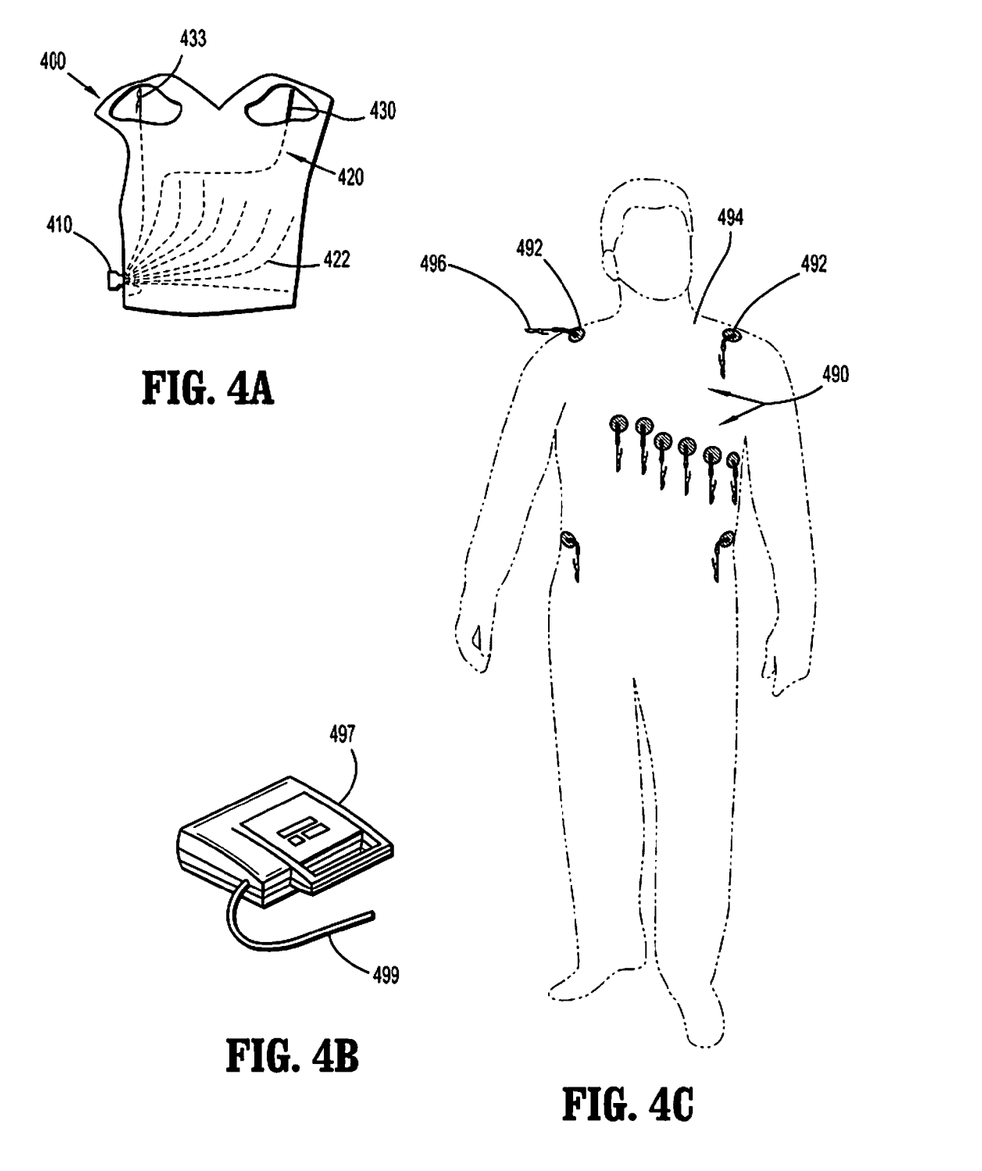
FIG. 4A is a front view of another embodiment of the present disclosure as a washable or disposable garment.
FIG. 4B is a front view of an electrode array and a monitoring, diagnostic or stimulating device for use with the garment of FIG. 4A.
FIG. 4C illustrates a subject with mounted electrodes cooperating with the device of FIG. 4B.

Referring now to FIG. 4A, an embodiment of a disposable or washable garment 400 is depicted, which may be used to reduce the risk of cross-infection from subject to subject. Near a lower end of the garment 400 is adapter 410, which is in electrical communication with each often signal transmission pathways 420. As discussed above with reference to preceding embodiments, each signal transmission pathway 420 is formed from a conductive thread 422 stitched into the garment 400. Conductive thread 422 is passed through garment 400 at appropriate intervals to affix the conductive thread 422 to the garment 400. Consequently, regular segments of the conductive thread 422 appear on the exterior side of the garment 400, while intermediate segments are concealed by the non conductive substrate of the garment 400. For this reason, signal transmission pathways 420 appear as dashed curved lines in FIG. 4A. Although a straight stitch is depicted in FIG. 4A, any stitching pattern may be selected.

Each signal transmission pathway 420 terminates at a connector 430, 433 on the interior of the garment 400. Each shoulder of garment 400 is shown broken to reveal the interior space containing the connector 430, 433. Connector 430 is simply formed as a minor lead segment by continuing conductive thread 422 a relatively short distance on the interior of garment 400. A connector 430 in this form facilitates laundering of the garment 400 and may be reinforced to withstand repeated laundering. Alternatively, connector 433 may be provided in the form of an alligator clip as shown. The alligator clip has a lead stitched onto garment 400 with the end of the conductive tread 422 forming the signal transmission pathway. A snap connector or any other convenient type of connector may be used for facilitating electrical coupling with a biomedical electrode such as the ECG electrodes depicted in FIG. 4B.

FIG. 4B depicts a biomedical electrode array 490 formed from ten ECG electrodes 492 arranged on a subject 494 (FIG. 4C) according to a standard 12-lead configuration. A lead of each electrode 492 is equipped with an alligator clip 496 and is in electrical communication therewith. Each alligator clip 496 is provided to facilitate electrical connection of electrode array 490 with a garment 400 having connectors 490 in the form of a minor lead segments. Alligator clips 496 may not be required if similar connectors 433 are provided on garment 400.

Also depicted in FIG. 4B is a monitoring, diagnostic or stimulating device 497 for monitoring the electrical signals received from electrodes 492. Monitoring, diagnostic or stimulating device 497 is equipped with cable 499 adapted to mechanically and electrically interface with adapter 410. When all necessary electrical connections are made, electrical continuity may be established from monitoring, diagnostic or stimulating device 497 to the subject 494 through cable 499, adapter 410, signal transmission pathways 420, connectors 430, alligator clips 496 and electrodes 492.

Figure 5:
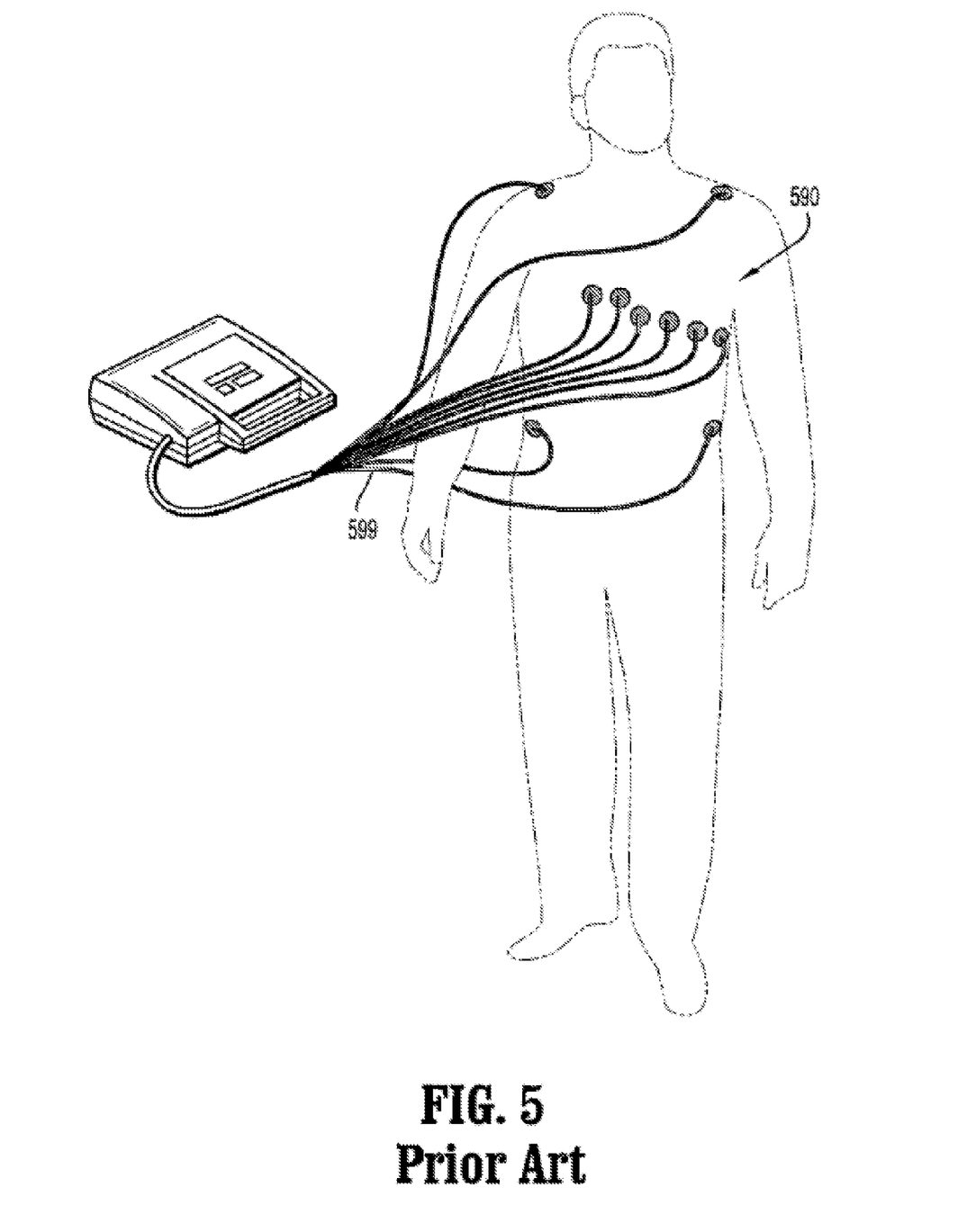
FIG. 5 is a front view of a standard 12-lead configuration of a traditional prior art ECG monitoring system.

A traditional prior art electrode array 590, as depicted in FIG. 5, is equipped with ten ECG electrode leadwires 599, commonly reusable from patient to patient Leadwires 599 may not be adequately cleaned between uses, increasing the risk of cross-infection. In this embodiment, the signal transmission pathways 420 may serve as ECG electrode lead wires. In contrast, in the embodiment shown in FIGS. 4A and 4B, garment 400 may be cleanable or disposable to reduce the risk of cross-infection from subject to subject. Additionally, stitching the conductive thread into garment 400 to form signal transmission pathways 420 replaces the cumbersome electrode leads 599 of traditional systems.

Although the foregoing disclosure has been described in some detail by way of illustration and example, for purposes of clarity or understanding, it will be obvious that certain changes and modifications may be practiced within the scope of the appended claims.

What is claimed is:

1. An apparatus for facilitating connection of a biomedical electrode array having one or more electrodes to a monitoring, diagnostic, or stimulating device, which comprises:
    a garment member for positioning relative to a body portion of a subject; and
    at least one signal transmission pathway comprising a conductive thread stitched into the garment member to affix the signal transmission pathway to the garment member, the at least one signal transmission pathway having a first end terminating at an aperture that extends through the garment member and connectable to an electrode, and a second end connectable to the monitoring, diagnostic, or stimulating device, the at least one signal transmission pathway adapted for transmitting signals between the electrode and the monitoring, diagnostic, or stimulating device.

2. The apparatus according to claim 1 wherein the first end is configured to be connectable to an ECG electrode.

3. The apparatus according to claim 1 including a plurality of signal transmission pathways stitched into the garment member for transmitting signals between respective electrodes and the monitoring, diagnostic or stimulating device.

4. The apparatus according to claim 3 including a connector coupled to the first end of each of the signal transmission pathways for connection to a respective electrode.

5. The apparatus according to claim 4 wherein at least one connector is in the form of a minor lead segment.

6. The apparatus according to claim 4 wherein at least one connector is in the form of an alligator clip.

7. The apparatus according to claim 1 including an adapter associated with the second end of the at least one transmission pathway, the adapter for electrical connection to the monitoring, diagnostic or stimulating device.

8. The apparatus according to claim 7 including a tab connected to the second end of the at least one signal transmission pathway, the tab adapted for electrical connection to the adapter.

9. The apparatus according to claim 1 including a fabric layer disposed adjacent to the at least one transmission pathway on an interior of the garment member.

10. The apparatus according to claim 9 wherein the fabric layer is an EMI shield layer.

11. The apparatus according to claim 1 wherein the garment member is a shirt or vest adapted for placement about the subject's torso.

12. The apparatus of claim 1 wherein the garment member is a sports bra.

13. The apparatus of claim 1 wherein the garment member comprises a non-conductive substrate covering intermediate segments of the conductive thread.

14. The apparatus of claim 1 further comprising a flap configured to cover at least a portion of the aperture and movable to permit access, through the aperture, to the electrode positioned on the subject's skin.

15. The apparatus of claim 14 comprising a connector mounted to the flap and in electrical connection with the first end of one of the at least one signal transmission pathway, the connector for connection to the electrode.

16. An apparatus for connection to a biomedical electrode array having a plurality of biomedical electrodes, which comprises:
    a garment member for positioning relative to a body portion of a subject and having at least one aperture providing access to one or more biomedical electrodes positionable on the subject;
    a plurality of signal transmission pathways having a first end terminating at the at least one aperture, each pathway comprising a conductive thread stitched into the garment member to affix the signal transmission pathway to the garment member, and each pathway adapted to transmit an electrical signal;
    a plurality of electrode connectors electrically coupled to the first ends of respective signal transmission pathways proximate to the at least one aperture, the electrode connectors adapted for connection to respective ones of the biomedical electrodes; and
    an adapter for electrically coupling the signal transmission pathways to an external monitoring or stimulating device.

17. The apparatus of claim 16 including a fabric layer disposed adjacent to the at least one transmission pathway on an interior of the garment member.

18. The apparatus of claim 17 wherein the fabric layer is also disposed on an exterior of the garment to at least partially cover the transmission pathway.

19. The apparatus according to claim 18 wherein the fabric layer is an EMI shield layer.

* * * * *